| United States Patent [19] | [11] | 4,053,531 |
|---|---|---|
| Kerr et al. | [45] | Oct. 11, 1977 |

[54] STEAM REFORMING OF POLYCYCLIC HYDROCARBONS

[75] Inventors: Edwin R. Kerr; Tansukhlal G. Dorawala, both of Wappingers Falls; Russell R. Reinhard, Hopewell Junction, all of N.Y.

[73] Assignee: Texaco Inc., New York, N.Y.

[21] Appl. No.: 617,911

[22] Filed: Sept. 29, 1975

[51] Int. Cl.² ........................... C07C 3/34; C07C 3/58
[52] U.S. Cl. ................... 260/672 R; 252/470; 252/474; 260/668 R
[58] Field of Search ............. 260/672 R, 668 R; 252/470, 474

[56] References Cited

U.S. PATENT DOCUMENTS

| 2,960,545 | 11/1960 | Seubold, Jr. | 260/672 R |
|---|---|---|---|
| 3,436,433 | 4/1969 | Lester | 260/672 R |
| 3,436,434 | 4/1969 | Lester | 260/672 R |
| 3,607,961 | 9/1971 | Kovach et al. | 260/672 R |
| 3,649,706 | 3/1972 | Lester | 260/672 R |
| 3,692,858 | 9/1972 | Brewer et al. | 260/672 R |
| 3,700,745 | 10/1972 | Kovach et al. | 260/672 R |
| 3,760,023 | 9/1973 | Patrick et al. | 260/672 R |
| 3,775,504 | 11/1973 | Sampson et al. | 260/672 R |

*Primary Examiner*—Daniel E. Wyman
*Assistant Examiner*—Thomas A. Waltz
*Attorney, Agent, or Firm*—Thomas H. Whaley; Carl G. Ries; Carl G. Seutter

[57] ABSTRACT

Polycyclic aromatic hydrocarbons are treated with steam in the presence of catalyst, typically containing oxides of nickel, potassium, chromium, and aluminum, to form aromatic products containing a lesser number of aromatic rings.

19 Claims, No Drawings

STEAM REFORMING OF POLYCYCLIC HYDROCARBONS

FIELD OF THE INVENTION

This invention relates to the conversion of hydrocarbons. More particularly, it relates to the treatment of alkyl polycyclic aromatic hydrocarbons, such as methyl naphthalenes.

BACKGROUND OF THE INVENTION

As is well known to those skilled in the art, polycyclic aromatic hydrocarbons have been subjected to conversion processes wherein a hydrocarbon is passed together with steam and hydrogen through a furnace at elevated temperatures and pressures to yield product. It is found that many such processes are less than fully satisfactory because of needed high pressures, need for use of hydrogen, generation of substantial quantities of undesired by-products, etc. Furthermore these processes provide very little reaction at aromatic rings.

It is an object of this invention to provide a process particularly characterized by operation at low pressures to produce desired products. Other objects will be apparent to those skilled in the art.

STATEMENT OF THE INVENTION

In accordance with certain of its aspects, the novel process of this invention for converting a charge polycyclic aromatic hydrocarbon to an aromatic product containing a lesser number of aromatic rings than said charge hydrocarbon charge may comprise passing a mixture of steam and a charge polycyclic aromatic hydrocarbon, at 850° F–1500° F, into contact with an activated supported catalyst containing oxides of (i) A Group VIB metal, (ii) a Group I A metal, and (iii) an after-deposited Group VIII metal, said supported catalyst containing Group VIII metal, expressed as metal oxide, in amount of at least about 0.5 wt % when said Group VIII metal is a noble metal and in amount of at least about 6 wt % when said Group VIII metal is iron, cobalt, or nickel, and at least about 15 % by weight of said Group VIII metal, expressed as oxide, being in the form of metal, thereby forming an aromatic product containing a lesser number of aromatic rings than said charge hydrocarbon; and recovering said product.

DESCRIPTION OF THE INVENTION

In accordance with certain of its aspects, the charge polycyclic aromatic hydrocarbon which may be treated by the process of this invention may be a stream typically having a boiling point of 350° F–1292° F (177° C–700° C). The stream may contain naphthalene hydrocarbons, either pure or in admixture, in varying quantities. This charge stream may typically contain alkyl naphthalenes such as 1-methyl napthalene, 2-methyl naphthalene, etc. The preferred charge hydrocarbon contains a methyl naphthalene; and in the preferred embodiment, it may be available as a stream from a lube oil extract or as a cycle stock recovered from a fluid catalytic cracking operation.

Typical charge streams which may be treated by the process of this invention may include those identified as a C-9 to C-16, preferably a C-9 to C-11 stream containing alkyl polycyclic aromatic hydrocarbons. Other charge streams may contain C-12 and higher polycyclic hydrocarbons or polyalkyl polycyclic hydrocarbons.

Illustrative of a typical charge stream may be a cracked cycle stock commonly containing the following components (by volume):

TABLE

| Component | Broad | Typical |
|---|---|---|
| C-8 and below | 0–5 | 0 |
| C-9 | 0–10 | 5 |
| C-10 | 30–60 | 45 |
| C-11 | 20–40 | 30 |
| C-12 and above | 10–30 | 20 |

Particularly desirable results may be achieved by use, as the hydrocarbon charge, of compositions containing substantial proportions of methyl naphthalene.

The supported catalyst which may be employed in practice of the process of this invention may comprise a catalyst support containing oxides of (i) a Group VI B metal, (ii) a Group I A metal and (iii) an after deposited Group VIII metal, said supported catalyst containing Group VIII metal, expressed as metal oxide, in amount of at least about 0.5 wt % when said Group VIII metal is a noble metal and in amount of at least about 6 wt % when said Group VIII metal is iron, cobalt, or nickel, and at least about 15% by weight of said Group VIII metal, expressed as oxide, being in the form of metal.

The Group VIII metal may include iron Fe, cobalt Co, nickel Ni, ruthenium Ru, rhodium Rh, palladium Pd, osmium Os, iridium Ir, and platinum Pt. Preferably the Group VIII metal may be nickel or cobalt; and in the most preferred embodiment, it is nickel. Although the Group VIII metal may be present in amounts down to 0.5% when it is a noble metal (i.e. Ru, Rh, Pd, Os, Ir, or Pt), it is preferred that the minimum be 6% when the Group VIII metal is Fe, Ni, or Co. Although it may be possible to have more than one metal of each of the Groups present (eg Ni and Pt) commonly only one such metal may be present.

The Group VI B metal may be chromium Cr, molybdenum Mo, or tungsten W; and in the preferred embodiment, it is chromium Cr.

The Group I A metal, an alkali metal, may be lithium Li, sodium Na, potassium K, rubidium Rb, or caesium Cs. In the preferred embodiment, it is potassium K.

The catalyst support may be active or inactive or inert. Typically the support may be a clay, a silica, a metal oxide, a zeolite, etc. The preferred porous materials may include alumina, silica, silica-alumina, silica-magnesia, silica-titania, silica-beryllia, silica-zirconia, silica-alumina-magnesia, etc. The preferred support is an inert support such as alumina, preferably gamma-alumina.

In typical practice of the process of this invention, the catalyst composition may contain the following components in the indicated parts by weight (expressed as oxide):

TABLE

| Component | Broad | Preferred | Typical |
|---|---|---|---|
| Group VIII Fe—Co—Ni or Ru—Rh—Pd Os—Ir—Pt | 6–40 0.5–10 | 6–20 0.5–5 | 15 1 |
| Group VI B | 0.01–40 | 10–38 | 15 |
| Group I A | 0.01–5 | 1–4 | 2 |
| Support | 15–99.5 | 38–88.5 | 68 |

The preferred catalyst may be that containing nickel-chromium-potassium-aluminum; and the catalyst composition may contain the following (expressed as oxide):

TABLE

| Component | Broad | Preferred | Typical |
|---|---|---|---|
| Ni | 6–40 | 6–20 | 15 |
| Cr | 0.01–40 | 10–38 | 15 |
| K | 0.01–5 | 1–4 | 2 |
| Al | 15–94 | 38–83 | 68 |

In terms of molar proportions, the catalyst may be represented by the formula $$a\,(VIII)_{2/n}O : b\,(VI)_{2/m}O : c\,(I)_2O$$

wherein (VIII) represents a metal of Group VIII of the Periodic Table having a valence $n$, (VI) represents a metal of Group VI B of the Periodic Table having a valence $m$, (I) represents a metal of Group I A of the Periodic Table. $a$ may be 0.002–0.75, preferably 0.002–0.38, say 0.20; $b$ may be 0.0001–0.78, preferably 0.13–0.75, say 0.29; and $c$ may be 0.00003–0.17, preferably 0.003–0.13, say 0.02.

In one preferred embodiment, the catalyst may be represented by the formula $$a\,NiO : b\,Cr_{2/3}O : c\,K_2O$$

wherein $a$ is 0.08–0.54, preferably 0.08–0.27, say 0.20; $b$ is 0.0002–0.78, preferably 0.21–0.75, say 0.29; and $c$ is 0.01–0.05 preferably 0.01–0.04, say 0.02.

When the support is alumina, as in the preferred embodiment, the catalyst composition may be represented by the formula $$a\,NiO : b\,Cr_{2/3}O : c\,K_2O : d\,Al_2O_3$$

wherein $a$, $b$ and $c$ are supra and $d$ is 0.15–0.93, preferably 0.38–0.81, say 0.67.

In practice of this invention, the catalyst may be prepared by immersing a catalyst support in a solution containing the metal ions. The support, typically a gamma-alumina extrudate of 1.5 mm diameter and 10 mm length may first be steam sintered at 900°–1400° F, say 1110° F for 5–25 hours, say 12 hours. During sintering, there may be passed through the bed air at VHSV (STP) of 40–600, say 230 together with steam at water VHSV of 0.05–0.10, say 0.06. The steamed alumina is then calcined for 1–5, say 2 hours at 900° F–1200° F say 1000° F. The initial surface of the alumina, typically 200–400, say 231 meter $^2$/gram may be decreased to 70%–95%, say about 90% to a value of 140–380, say 192 meter $^2$/gram.

The support (242 parts), preferably as so treated, is cooled to 32° F–80° F, say about 32° F and wetted with 200–2525 parts, say 890 parts of solution prepared by dissolving soluble decomposable salts of metals of Group VI B and Group I A in aqueous solution. Preferably 5–1000 parts, more preferably 200–1000, say 792 parts of salt of Group VI B metal, typically chromium nitrate nonahydrate Cr (NO$_3$)$_3$.9H$_2$O and 5–25 parts, preferably 10–23, say 17.2 parts of salt of Group I A metal, typically potassium nitrate are dissolved in 10–1500 parts, say 80 parts of water to yield total solution in amount of 15–2525 parts, say 890 parts. (Although nitrates of the metals are preferably employed, acetates, formates, citrates, or other soluble, decomposable salts may be used).

The solution is poured over the support and is stirred intermittently for 0.5–10 hours, say 1 hour and the solution (50–2400 parts, typically 731 parts) may then be decanted. The impregnated support is dried at 212° F–400° F, say 300° F, then heated to decomposition temperature of typically 650° F–1000° F, say 700° F, and calcined for 1–10 hours, say 2 hours at 700° F–1400° F, say 1000° F. This procedure is preferably repeated 2–4, preferably 2 times more until all the metal salt solution is absorbed by the support. The final pre-catalyst so prepared in amount of 242–1500 parts, say 383 parts may be characterized by the formula $$b\,(VI)_{2/m}O \cdot c\,(I)_2O \cdot d\,Al_2O_3$$

wherein (VI) represents a metal having valence $m$ of Group VI B of the Periodic Table, (I) represents a metal of Group I A of the Periodic Table, $b$ is 0.0001–0.78, preferably 0.13–0.75, say 0.74, $c$ is 0.000.1–0.17, preferably 0.011–0.13, say 0.02, and $d$ is 0.15–2.49, preferably 0.38–0.81, say 0.59. (Supports other than or in addition to Al$_2$O$_3$ may be present).

In one preferred embodiment, the composition of the pre-catalyst may be $$b\,Cr_1O : c\,K_2O : d\,Al_2O_3$$

where $b = 0.25, c = 0.02, d = 0.59$. 292–1500 parts, say 383 parts of pre-catalyst may be cooled to 32° F–80° F, say 32° F and impregnated with an after-deposited decomposable soluble salt of a Group VIII metal. Preferably the solution may contain 50–700 parts, say 267 parts of Ni(NO$_3$)$_2$.6H$_2$O in 50–1400 parts, say 263 parts of water. After 0.5–10 hours, say 1 hour of intermittent stirring, the excess non-absorbed solution is decanted and the solids dried for 2–18 hours, say 16 hours at 212° F–400° F, say 300° F. The dried solid is reimpregnated with the remaining salt solution for 0.5–10 hours, say 1 hour and dried again for 2–18 hours, say 16 hours at 212° F–400° F, say 300° F. Further treatment includes heating for 0.5–24 hours, say 1 hour, at 650° F–1000° F, say 700° F in a flowing stream of air to decompose the decomposable salts, typically nitrates, and then calcining for 1–10 hours, say 2 hours at 600° F–1000° F to yield 260–1850 parts, say 462 parts having a density of 0.7–1.5, say 1.11.

The product catalyst so prepared may be characterized by the formula $$a\,(VIII)_{2/n}O : b\,(VI)_{2/m}O : c\,(I)_2O : d\,(Sup)$$

wherein all the symbols are as noted supra except that $a$ is 0.002–0.75, preferably 0.002–0.38, say 0.20, (VIII) represents a metal, having a valence $n$, of Group VIII of the Periodic Table, preferably nickel, and (Sup) represents the catalyst support, preferably Al$_2$O$_3$.

Preferred catalyst compositions may have the formulae:

$$0.25\,NiO : 0.27\,Cr_1O : 0.02\,K_2O : 0.64\,Al_2O_3$$

$$0.17\,NiO : 0.65\,Cr_1O : 0.02\,K_2O : 0.51\,Al_2O_3$$

$$0.20\,CoO : 0.20\,Cr_1O : 0.02\,Na_2O : 0.34\,SiO_2$$

Expressed on a weight basis, the catalyst may have the composition set forth in the following Table:

| Component | Broad | Preferred | Typical |
|---|---|---|---|
| $(VIII)_{2/n}O$ | 0.5–40 | 0.5–20 | 15 |

-continued

| Component | Broad | Preferred | Typical |
|---|---|---|---|
| Fe—Co—Ni or Ru—Rh—Pd | 6-40 | 6-20 | 15 |
| Os—Ir—Pt | 0.5-10 | 0.5-5 | 1 |
| $(VI)_2O$ | 0.01-40 | 10-38 | 15 |
| $(I)_2O$ | 0.01-5 | 1-4 | 2 |
| (Sup) | 15-99.5 | 38-84 | 68 |

A preferred composition may contain 17.7% NiO, 13.2% $Cr_2O_3$, 1.9% $K_2O$, and 61.6% $Al_2O_3$. Another preferred composition may contain 11.9% NiO, 30.4% $Cr_2O_3$, 1.4% $K_2O$, and 48.2% $Al_2O_3$ — percentages in this paragraph being on a weight basis.

The catalyst composition of this invention may be prepared by impregnating the support with solutions of metals of Groups VIII, VIB, and IA. Typically for example it may be found that the catalyst may be prepared by:

a. impregnating the support sequentially with several solutions each containing one or more of the metals and thereafter drying and calcining;

b. impregnating the support with one or more solutions containing less than all of the metals (i.e. species or amount), drying and/or calcining, therafter impregnating the support with the remaining metals, and drying and/or calcining; etc.

It is unexpectedly found however that substantially superior results are achieved (in terms of conversion, yield, and/or selectivity) if the Group VIB and IA metals are impregnated, dried, and calcined on the catalyst support prior to the impregnation thereof with the Group VIII metal.

In the preferred embodiment, the catalyst support may thus be prepared by impregnating the support, typically alumina, with one solution containing soluble decomposable salts of the Group VIB and Group IA metals, typically chromium and potassium, drying and calcining, thereafter impregnating the so-obtained pre-catalyst with a solution of a soluble decomposable salt of the Group VIII metal, typically nickel, and drying and calcining. Catalyst containing the after-deposited Group VIII metal (i.e. the Group VIII metal deposited after the Group VI B and Group I A metals are present with the support) are particularly characterized by high yields of product.

Preferably at least a portion of the Group VIII metal (more preferably a major portion e.g. greater than 50% is after-deposited.

In the preferred embodiment, the catalyst composition may be in the form of pellets, cylinders, or randomly shaped particles; a typical catalyst composition may be in the form of cylinders, of diameter 1-15 mm, say 1.5 mm and height 1-15 mm, say 8-10 mm.

It is a feature of the preferred catalyst of this invention that it be activated prior to use. Preferably activation may be carried out by the process which comprises a. maintaining the unactivated catalyst in a hydrogen atmosphere at 750° F-1400° F, say 1100° F for 10-30 hours thereby forming a hydrogen-treated catalyst;

b. maintaining the hydrogen-treated catalyst in a steam-hydrogen atmosphere at 750° F-1400° F say 1100° F for 2-10 hours thereby forming a steamed hydrogen treated catalyst; and c. preferably cooling the activated steamed hydrogen-treated catalyst to operating temperature of 850° F-1400° F, say 950° F for 1-10 hours in a steam or steam-hydrogen atmosphere thereby forming an activated catalyst.

Activation of the catalyst may preferably be carried out after the catalyst is in place in the reaction vessel. The vessel may be filled with catalyst composition to a bed bulk density of 50-80 pcf, say 70 pcf. In the first portion of the activation operation, the catalyst composition is heated to 750° F-1400° F, preferably 900° F-1100° F in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components including oxygen.

The gas may contain (in addition to hydrogen) helium or more preferably light paraffins such as methane, ethane, propane, etc. Hydrogen may be present typically in amount of 30 mole % - 100 mole %, preferably 80 mole % — 100 mole %, say 100 mole %, i.e. the preferred embodiment may be that in which the gas consists essentially of hydrogen.

Preferably the catalyst composition may be maintained for 10-30 hours, typically 14-16 hours, say 15 hours in a stream of flowing hydrogen typically flowing at a space velocity VHSV (STP) greater than about 3, more preferably greater than 100, say 100-500, typically 300.

When activation is carried out at atmospheric pressure, as in the preferred embodiment, the partial pressure of hydrogen may be at least about 9 psia (400 mm Hg), preferably 12-15 psia, say 15 psia (760 mm Hg).

In the preferred second portion of the activation cycle, the hydrogen-treated catalyst may be maintained at 750°-1400° F, preferably 900° F-1100° F, say 1100° F (most preferably at about the same temperature as that employed in the first portion) in a flowing stream of hydrogen and steam. This stream may contain 15-50 mole %, preferably 20-40 mole %, say 30 mole % of hydrogen, 50-85 mole %, preferably 60-80 mole %, say 70 mole % of steam, and 0-10 mole %, preferably 0-5 mole %, say about 0 mole % of inert gas such as helium, nitrogen, or light paraffins. Preferably the gas may consist essentially of hydrogen and steam in molar ratio of 0.2-1, typically 0.25-0.67, say 0.42.

When activation is carried out at atmospheric pressure, as in the preferred embodiment, the partial pressure of hydrogen may be 100-380, preferably 150-300, say 240 mm Hg; and the partial pressure of steam may be 380-660, preferably 460-610, say 520 mm Hg.

The third portion of the activation procedure may be carried out for 2-10 hours, preferably 2-5 hours, say 2 hours in a stream of flowing gas at a space velocity VHSV (STP) greater than about 1.5, preferably greater than 50, say 50-250, typically 150.

Post activation cooling or heating is typically carried out by maintaining the activated catalyst in a stream of flowing steam for 1-10 hours, preferably 1-5 hours, say 2 hours as the temperature is lowered to operating temperature of 850° F-1500° F, preferably 850° F-1200° F, say 950° F. Preferably steam is present during post-activation in amount of 50-100 mole %, typically 80-100 mole %, say about 100 mole % of the flowing stream.

It is a feature of the catalyst of this invention that, in the activated form, it is characterized by the presence of Group VIII metal, preferably nickel, in the form of metal. The catalyst as prepared contains Group VIII metal as oxide; and this oxide must be reduced at least in part prior to use as catalyst. Reduction, during activation, is sufficient to reduce at least a portion of the Group VIII metal oxide to metal. The activated or reduced catalyst may normally contain eg 15 - 100 mole percent, preferably 50-100 mole percent, say 70 mole percent of the Group VIII metal in the form of metal and the remainder in a combined form such as the oxide or aluminate.

Thus the activated or reduced catalyst may be characterised by the formula:

$$x(VIII) : (a-x) (VIII)_{2/n}O : b (VI)_{2/m}O : d (Sup)$$

wherein the symbols $a$, $b$, $c$, and $d$ are as noted supra and $x$ is 0.0003-0.75, preferably 0.001-0.38, say 0.14. This is equivalent to saying that activation has reduced a portion of the oxide of the Group VIII metal to the free metal; and the free metal is present in mole percent of preferably 50%-100%, say 70% of the total of metal plus oxide.

In the preferred embodiment, the activated catalyst may be

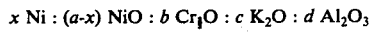

$$x \text{ Ni} : (a-x) \text{ NiO} : b \text{ Cr}_t\text{O} : c \text{ K}_2\text{O} : d \text{ Al}_2\text{O}_3$$

where $x$ is 0.01-0.54, preferably 0.04-0.27, say 0.14 and the other values are as above. In this instance, this is equivalent to saying that of the total nickel content of metal and oxide, 15%-100%, preferably 50%-100%, say 70% by weight is in the form of nickel metal.

It is a feature of the catalysts of this invention that measurement of the surface area of the free Group VIII metal present reveals that the process of this invention may be carried out to give conversions above about 40%, when that surface area is greater than about 8 square meters per gram of total activated catalyst composition. Preferably the surface area may be 8-30, say 24 square meters per gram as determined by the nickel metal content (by intensity of the diffraction line) and metallic nickel weight average crystal size.

Treatment of the hydrocarbon charge may be carried out by passing the charge at 850° F-1500° F preferably 950° F-1200° F, say 950° F and pressure of 0-400 psig, preferably 0-200 psig, say 0 psig together with steam in amount of 1-25 moles, preferably 1-15 moles, say 10 moles per mole of hydrocarbon charge (corresponding to 100-1250% preferably 10%-750%, say 150% of the stoichiometric quantity) to a reaction zone. In commercial practice it may be desirable to operate at super atmospheric pressure.

During reaction at these conditions, alkyl groups are removed from the charge alkyl polycyclic aromatic hydrocarbons to form product hydrocarbons bearing lesser numbers of alkyl groups on the aromatic nuclei. Simultaneously an aromatic ring may be ruptured and the residue split off to form an aromatic product containing a lesser number of aromatic rings than the charge. When the charge hydrocarbon contains methyl naphthalene, the product stream may typically contain naphthalene, xylenes, toluene, benzene, etc. In addition, the product stream may contain unreacted charge hydrocarbons, hydrogen, oxides of carbon, and lesser amounts of low molecular weight paraffins (eg methane) in addition to other by-products. The cracked product typically contains cracked components corresponding to a rupture of at least one aromatic ring in at least about 50% of the charge molecules.

Product hydrocarbon may be withdrawn from the reaction vessel and condensed. The liquid condensate may represent a recovery of 50-100 weight %, preferably 70-96 weight %, say 73 weight % of the hydrocarbon charged.

In the case of a pure 1-methyl naphthalene charge for example, the product (moles per 100 moles of charge) may contain the following:

TABLE

| Component | Broad | Preferred | Typical |
|---|---|---|---|
| Unreacted charge | 20-90 | 30-85 | 57 |
| naphthalene | 1-40 | 5-35 | 27 |
| benzene | 0.1-50 | 0.3-30 | 8 |
| toluene | 0.01-10 | 0.4-8 | 3 |
| xylene | 0.1-10 | 0.4-4 | 1 |
| gases | 20-1000 | 33-750 | 340 |

In practice of the process of this invention according to the preferred embodiment, the reaction is carried out on a short cycle basis; i.e. the reaction proper (with a charge of steam and hydrocarbon) is carried out for 0.5-3.0 minutes, preferably 0.5-2.0 minutes, say 1 minute and then the catalyst is regenerated by shutting off the flow of hydrocarbon (and contacting it with the hydrocarbon-free steam) for 0.5-15 minutes, preferably 1-8 minutes, say 3 minutes. The ratio of regeneration time to reaction time may be 1-5, preferably 2-4, say 3.

It is found during practice of the process of this invention that it is possible to achieve improved catalyst activity. For example the conversion (in terms of mole percent of polynuclear aromatic charge) may be 40%-95%, typically 40-80%, say 68% in the preferred embodiment.

It is also a feature of the process of this invention in its preferred embodiment that it permits attainment of BTX yield (in terms of mole percent of the polynuclear aromatic charge) which may be 8%-60%, typically 10-40%, say 28%.

The novel process permits attainment of these conversions and yields with a high selectivity. The selectivity to BTX (in terms of mole percent of the polynuclear aromatic charge stream converted) may approach 65% and may commonly be 20% -65%.

The catalyst is characterized by increased steam stability and durability. Although it may be found that the crush strength (in pounds) of the alumina support may decrease by as much as 50% during steaming, it is unexpectedly found that the crush strength of the catalyst of this invention (with an alumina support) is essentially equal to the crush strength of fresh alumina support; and this crush strength (and the surface area of the catalyst) may unexpectedly remain essentially constant or increase during steaming.

It is also a feature of the catalyst of this invention that it is possible to achieve these desirably improved novel results by use of a catalyst composition which unexpectedly contains such a low concentration of nickel. Typically the catalyst composition of this invention contains about 6%-40%, preferably 6%-20%, say 15% by weight of nickel oxides. The ability to obtain outstanding results by use of a catalyst containing such low amounts of nickel permits substantial savings in capital costs in terms of cost of nickel.

It is found however that practice of the process of this invention is achieved if the concentration of Group VIII metal (typically as nickel) is above about 6% by weight (i.e. when expressed as nickel oxide). Nickel content below this level yields undesirably low conversion. Although when the Group VIII metal is Fe, Co, or Ni, it may be desirable to increase the concentration up to about 20%, satisfactory results are commonly attainable at 6% -10%.

It is particularly unexpected that alkyl polycyclic aromatic hydrocarbons may be readily converted at mild conditions, typically at atmospheric pressure in the absence of added hydrogen, to form a product stream containing aromatic products having a lesser number of aromatic rings than the charge hydrocarbon. It is particularly unexpected that one can readily convert methyl naphthalene to a desired BTX stream under such mild conditions.

DESCRIPTION OF THE PREFERRED EMBODIMENTS

Practice of the process of this invention will be apparent to those skilled in the art from the following illustrative embodiments wherein, as elsewhere in this description, all parts are parts by weight unless otherwise specifically stated.

EXAMPLE I

In this example, a catalyst is prepared corresponding to the formula $$0.25\ NiO : 0.27\ Cr_{2/3}O : 0.02\ K_2O : 0.64\ Al_2O_3$$

and containing 17.7% $NiO$, 13.2% $Cr_2O_3$, 1.9% $K_2O$, and 61.6% $Al_2O_3$.

The catalyst support is gamma-alumina in the form of cylinders of average height 10 mm and diameter 1.5 mm (Aero 100 brand product of American Cyanamid) and it possesses a surface area of 231 square meters per gram. The support is steam sintered in a stainless steel tubular reactor by heating to 1110° F for 12 hours while in contact with a moving stream containing 64 g/hr of water and 8.0 cubic feet per hour of air. After 12 hours, the steam is shut off and the alumina is calcined at 1000° F for 2 hours in a stream of air (8.0 cubic feet per hour). The surface area of the calcined alumina is 192 m $^2$/g.

In the first portion of this example 340 parts of calcined alumina are soaked with a solution prepared by dissolving 395 parts of chromium nitrate nonahydrate and 21.5 of potassium nitrate in 1000 parts of water. After one hour, the remaining solution is decanted and the impregnated support is dried at 300° F, nitrate-decomposed at 700° F, and calcined for 2 hours at 1000° F. 424 parts of pre-catalyst is thus obtained.

In this second portion of this example, 293 parts of this pre-catalyst is cooled to 32° F and impregnated with a solution of 256 parts of nickelous nitrate hexahydrate in 500 parts of water. The excess solution is decanted.

The catalyst is dried at 300° F, and the cooled catalyst is reimpregnated with the remaining solution and dried again at 300° F. The catalyst is then nitrate-decomposed in air at 700° F for 2 hours and calcined further in air at 700° F for 2 hours. The product catalyst composition (362 parts of density 0.9) corresponds to the formula $$0.25\ NiO : 0.27\ Cr_{2/3}O : 0.02\ K_2O : 0.64\ Al_2O_3$$

and contains 17.7% $NiO$, 13.2% $Cr_2O_3$, 1.9% $K_2O$, and 61.6% $Al_2O_3$.

EXAMPLE II -IV

In each of these comparative examples, 75 ml of catalyst (67 grams) is charged to a fixed bed tubular reactor (2.5 cm diameter × 46 cm long vertically mounted with inlet at top). The catalyst is centered in the reactor by Berl saddles (6 mm). Activation is effected by heating to 1100° F in the presence of flowing (1 liter per minute) hydrogen, holding at 1100° F for 16 hours in 0.5 liters per minute of hydrogen, and then holding at 1100° F for 2 hours in 70-80g of steam per hour plus 0.5 liters per minute of hydrogen. At the end of this period, the hydrogen flow is turned off; and the reactor temperature is lowered to reaction temperature in the presence of steam alone.

At this time hydrocarbon pump was turned on and the data noted in the following table was taken on a short cycle basis. This is effected by a 1 minute reaction period during which steam and methyl naphthalene (purissima grade — Aldrich Chem. Co.) are charged followed by a 3 minute regeneration period during which steam alone is charged. In each instance a preliminary period of 30 minutes is allowed to pass; and the product is collected over 45 minutes.

Runs were carried out at Me Nap (methyl naphthalene) space velocity WHSV of 0.5, based upon total of reaction plus regeneration time. The steam WHSV was 0.5 on the same basis. 1.7 moles of steam per mole of methyl naphthalene were charged during the reaction portion of the cycle.

There are tabulated in the following table, the temperature of operation °F; the liquid hydrocarbon recovered in terms of weight percent of the 1-methyl naphthalene charged; the overall material balance in terms of percent of the charge accounted for; the mole percent of MeNap converted to other products; the yield and selectivity, in mole percent, for benzene, toluene, xylenes, naphthalene, and total liquid products; and the off-gas analysis, in terms of mole percent, of hydrogen, methane, carbon monoxide, and carbon dioxide.

|  | II* | III* | IV* | V | VI | VII |
|---|---|---|---|---|---|---|
| Temperature, ° F | 650 | 725 | 805 | 875 | 875 | 950 |
| Liquid Hydrocarbon Recovery, Wt % 1-MeNap Charged | 95 | 96 | 92 | 90 | 86 | 73 |
| Overall Material Balance | 92 | 94 | 97 | 94 | 90 | 94 |
| MeNap Conversion, mole % MeNap Charged | 15 | 19 | 37 | 42 | 44 | 68 |
| Yield, mole % MeNap Charged |  |  |  |  |  |  |
| Benzene | 0.3 | 1.0 | 3.2 | 7.5 | 9.0 | 23.0 |
| Toluene | 0.4 | 0.9 | 2.3 | 2.5 | 3.1 | 4.5 |
| Xylenes | 3.9 | 1.0 | 0.7 | 0.7 | 0.8 | 0.4 |
| Naphthalene | 6.5 | 15.3 | 28.4 | 28.0 | 25.6 | 28.2 |
| Total Liquid Products | 11.1 | 18.2 | 34.6 | 38.7 | 38.5 | 56.1 |
| Selectivities, Yield/Conversion |  |  |  |  |  |  |
| to Benzene | 2.4 | 5.5 | 8.7 | 18.1 | 20.3 | 33.7 |
| to Toluene | 3.0 | 4.6 | 6.2 | 6.0 | 6.9 | 6.7 |
| To Xylenes | 27.2 | 5.3 | 2.0 | 1.7 | 1.8 | 0.6 |
| to Naphthalene | 45.0 | 79.1 | 76.9 | 67.4 | 57.8 | 41.4 |

-continued

|  | II* | III* | IV* | V | VI | VII |
|---|---|---|---|---|---|---|
| to Total Liquid Products | 77.6 | 94.5 | 93.8 | 93.2 | 86.9 | 82.4 |
| Off-Gas Analysis, Mole % |  |  |  |  |  |  |
| Hydrogen | 75.5 | 73.3 | 72.3 | 70.4 | 70.4 | 68.7 |
| Methane | 0.1 | 0.1 | 0.1 | 0.4 | 0.4 | 0.4 |
| CO | 1.2 | 2.0 | 3.0 | 4.4 | 4.4 | 7.9 |
| $CO_2$ | 23.2 | 24.5 | 24.6 | 24.8 | 24.8 | 23.1 |

*Control runs

From the above table it will be apparent that the novel process of this invention permits ready conversion of charge alkyl polycyclic hydrocarbons to aromatic products containing a lesser number of aromatic rings. Specifically for example methyl naphthalene may be converted to product streams at atmospheric pressure and at preferred temperature of 950° F; and the product stream is characterized by 68 mole percent methyl naphthalene conversion. From control Examples II, III and IV, conducted at 650° F, 725° F, and 805° F which are below the preferred temperature range of 850° F–1500° F, it will be apparent that the conversion of charge is below about 40% which is undesirably low — down to only 15%. In contrast, Example VII at the preferred temperature gives conversion of 68%. In control runs II–IV, the yield of BTX is 4.6 – 2.9 – 6.2 in comparison to Experimental Examples V – VI – VII which show yield of 10.7 – 12.9 – 27.9. Even more outstanding results are achieved in terms of selectivities. It is possible to achieve these desired results with simultaneous production of off-gas containing substantial quantities of hydrogen which may readily be separated and utilized.

It is particularly unexpected that one is able to effect substantial conversion of an alkyl polycyclic aromatic compound to eg BTX products — one skilled in the art would expect that the catalyst of this process would not be sufficiently severe to rupture an aromatic ring.

Results comparable to those obtained in the above examples may be obtained by using as charge stream:

a. a cycle stock (obtained as bottoms after removal of gasoline and lighter fractions from the effluent of a fluid catalytic cracking operation) having the following properties:

TABLE

| Gravity ° API | 28.4 |
|---|---|
| Boiling Range ° F |  |
| IBP | 350 |
| 50% | 434 |
| 90% | 513 |
| Saturates Vol % | 34.5 |
| Olefins Vol % | 4.0 |
| Aromatics Vol % | 61.5 |
| Composition of Aromatics vol% |  |
| Alkylbenzenes | 32.0 |
| Indanes & tetralins | 28.1 |
| Indenes | 2.8 |
| Naphthalenes | 33.2 |
| Acenaphthenes and Acenaphthylenes | 3.4 |
| Tricyclic Aromatics | 0.5 | b. a stream obtained from lube oils by extraction with furfural and having the following properties:

TABLE

| Gravity ° API | 16.9 |
|---|---|
| Pour ° F | 60 |
| Boiling Range ° F |  |
| IBP | 575 |
| 50% | 790 |
| 90% | 850 |
| Saturates vol % | 47.6 |
| Aromatics vol % | 52.4 |
| Composition of Aromatics vol % |  |

TABLE-continued

| Benzenes | 27.3 |
|---|---|
| Tetralins, indanes, octahydrophenanthrenes | 24.2 |
| Naphthalene | 11.0 |
| Diphenyls, acenaphthenes | 10.9 |
| Phenanthrenes, tetrahydrochrysenes | 9.2 |
| Pyrenes | 7.3 |
| Chrysenes, benzanthracenes | 7.3 |
| Perylenes, 5-ring condensed aromatics | 2.9 |

These results may also be achieved when the catalyst contains other proportions of components and other components. For example, the support may be silica-magnesia, silica-alumina etc. in place of alumina. The Group VIII metal may be cobalt. The Group VIB metal may by molybdenum or tungsten. The group IA metal may be sodium etc.

Although this invention has been illustrated by reference to specific embodiments, it will be apparent to those skilled in the art that various changes and modifications may be made which clearly fall within the scope of this invention.

We claim:

1. The process for converting a charge polycyclic aromatic hydrocarbon to an aromatic product containing a lesser number of aromatic rings than said charge hydrocarbon which comprises passing a mixture of steam and a charge polycyclic aromatic hydrocarbon at 850° F–1500° F and 0–400 psig into contact with an activated supported catalyst containing oxides of (i) a Group VIB metal, (ii) a Group I A metal, and (iii) an after-deposited Group VIII metal, said supported catalyst containing Group VIII metal, expressed as metal oxide, in amount of at least about 0.5 wt % when said Group VIII metal is a noble metal and in amount of at least about 6 wt % when said Group VIII metal is iron, cobalt, or nickel, and at least about 15% by weight of said Group VIII metal, expressed as oxide, being in the form of metal thereby forming an aromatic product containing a lesser number of aromatic rings than said charge hydrocarbon; and recovering said product.

2. The process as claimed in claim 1 wherein said Group VIII metal is nickel or cobalt.

3. The process as claimed in claim 1 wherein said Group VIII metal is nickel.

4. The process as claimed in claim 1 wherein said Group VI B metal is chromium.

5. The process as claimed in claim 1 wherein said Group I A metal is potassium.

6. The process as claimed in claim 1 wherein said support contains alumina.

7. The process as claimed in claim 1 wherein said catalyst contains 6%–20% by weight of iron, cobalt, or nickel (expressed as oxide).

8. The process as claimed in claim 1 wherein said Group VIII metal is ruthenium, rhodium, osmium, iridium, palladium, or platinum present in amount of 0.5%.

9. The process as claimed in claim 1 wherein said catalyst contains Group VIII metal present in amount of 0.5-10 parts as Ru, Rh, Pt, Os, Ir, or Pt or in amount of 6-40 parts as Fe, Co, or Ni, 0.01-40 parts of Group VI B metal, 0.01-5 parts of Group I A metal, and 15-99.5 parts of support — all parts being expressed as oxides.

10. The process as claimed in claim 1 wherein said catalyst is $$a\,(VIII)_2O : b(VI)_2O : c\,(I)_2O : d\,(Sup)$$

wherein (VIII) represents a metal of Group VIII of the periodic table of valence $n$, (I) represents a metal of Group I A of the periodic table, (VI) represents a metal of Group VI B of the periodic table of valence $m$, $a$ is 0.002-0.75, $b$ is 0.0001-0.78, $c$ is 0.00003-0.17, $d$ is 0.15-2.49 and (Sup) represents the support.

11. The process as claimed in claim 1 wherein said catalyst is $$a\,NiO : b\,Cr_{2/3}O : c\,K_2O : d\,(Sup)$$

wherein $a$ is 0.08-0.54, $b$ is 0.0002-0.78, $c$ is 0.01-0.05, $d$ is 0.15-2.49 and (Sup) represents the support.

12. The process as claimed in claim 1 wherein said catalyst is $$(0.08-0.27)NiO:(0.21-0.67)Cr_{2/3}O:(0.01-0.04)K_2O:(0.38-0.81)Al_2O_3.$$

13. The process as claimed in claim 1 wherein said catalyst is $$0.25 NiO : 0.27\,Cr_{2/3}O : 0.02\,K_2O : 0.64\,Al_2O_3.$$

14. The process as claimed in claim 1 wherein said charge polycyclic aromatic hydrocarbon contains a $C_9$ to $C_{16}$ hydrocarbon fraction.

15. The process as claimed in claim 1 wherein said charge polycyclic aromatic hydrocarbon contains a hydrocarbon fraction having at least 9 carbon atoms.

16. The process as claimed in claim 1 wherein said charge polycyclic aromatic hydrocarbon contains a methylnaphthalene fraction.

17. The process for converting a charge $C_9$ to $C_{16}$ polycyclic aromatic hydrocarbon to an aromatic product containing a Benzene-Toluene-Xylene fraction which comprises passing a mixture of steam and charge $C_9$ to $C_{16}$ polycyclic aromatic hydrocarbon at 850° F-1500° F and 0-400 psig into contact with an activated supported catalyst containing oxides of chromium, potassium, and nickel — said nickel having been deposited on said support after said chromium and potassium - said nickel being present in amount of at least 6 wt % of said catalyst and at least about 15% of the nickel, expressed as oxide, being in the form of nickel metal thereby forming aromatic product containing a BTX fraction; and recovering said product.

18. The process for converting a charge $C_9$ to $C_{16}$ polycyclic aromatic hydrocarbon to an aromatic product containing a Benzene-Toluene-Xylene fraction which comprises passing a mixture of steam and charge $C_9$ to $C_{16}$ polycyclic aromatic hydrocarbon at 850° F-1500° F and 0-400 psig into contact with an activated supported catalyst containing oxides of chromium, potassium, and nickel — said nickel having been deposited on said support after said chromium and potassium — said nickel being present in amount of at least 6 wt % of said catalyst and at least about 15% of the nickel, expressed as oxide, being in the form of nickel metal thereby forming aromatic product containing a BTX fraction;

maintaining said flow of steam and charge hydrocarbon in contact with said catalyst during a reaction period of 0.5-3 minutes during which period catalyst becomes deactivated;

thereafter decreasing the flow of hydrocarbon charge during a regeneration period of 0.5-15 minutes during which period the catalyst is regenerated;

subjecting said catalyst to at least one reaction period and at least one regeneration period; and recovering said product formed during a reaction period.

19. The process as claimed in claim 18 wherein said flow of hydrocarbon charge is substantially stopped during said regenerating period.

* * * * *

UNITED STATES PATENT AND TRADEMARK OFFICE
CERTIFICATE OF CORRECTION

PATENT NO. : 4,053,,531
DATED : October 11, 1977
INVENTOR(S) : Kerr et al

It is certified that error appears in the above–identified patent and that said Letters Patent are hereby corrected as shown below:

Col. 13, line 3, cancel "Pt" second occurrence, insert -- Pd --;

Col. 13, line 10, correct the formula to read as follows:

$$\underline{a}\ (VIII)_{2/n}O\ :\ \underline{b}\ (VI)_{2/m}O\ :\ \underline{c}\ (I)_2O\ :\ \underline{d}\ (Sup)$$

Col. 13, lines 28-29, please correct the formula to read as follows:

$(0.08-0.27)NiO:(0.21-0.67)Cr_{2/3}O:(0.01-0.04)K_2O:(0.38-0.81)Al_2O_3$

Signed and Sealed this

Thirtieth Day of October 1979

[SEAL]

Attest:

RUTH C. MASON
Attesting Officer

LUTRELLE F. PARKER
Acting Commissioner of Patents and Trademarks